(12) United States Patent
Lee et al.

(10) Patent No.: US 9,441,251 B2
(45) Date of Patent: Sep. 13, 2016

(54) VARIANT MICROORGANISM ABLE TO PRODUCE LARGE AMOUNT OF FERMENTATION PRODUCT, AND FERMENTATION PRODUCT PRODUCTION METHOD USING SAME

(71) Applicant: Korea Research Institute of Bioscience and Biotechnology, Daejeon (KR)

(72) Inventors: Sang Jun Lee, Daejeon (KR); Hyun Ju Kim, Daejeon (KR); Dong-Woo Lee, Daejeon (KR); Joong Su Kim, Daejeon (KR); Haeyoung Jeong, Daejeon (KR); Bo Kyeng Hou, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 14/398,430

(22) PCT Filed: Jun. 14, 2013

(86) PCT No.: PCT/KR2013/005285
§ 371 (c)(1),
(2) Date: Jan. 30, 2015

(87) PCT Pub. No.: WO2013/187733
PCT Pub. Date: Dec. 19, 2013

(65) Prior Publication Data
US 2015/0211031 A1    Jul. 30, 2015

(30) Foreign Application Priority Data
Jun. 15, 2012    (KR) .................. 10-2012-0064525

(51) Int. Cl.
*C12N 1/20*    (2006.01)
*C12N 15/00*    (2006.01)
(Continued)

(52) U.S. Cl.
CPC . *C12P 7/56* (2013.01); *C12N 1/20* (2013.01); *C12N 15/01* (2013.01); *C12N 15/09* (2013.01); *C12P 7/06* (2013.01); *C12P 7/46* (2013.01); *Y02E 50/17* (2013.01)

(58) Field of Classification Search
CPC ............ C12P 7/56; C12N 1/20; C12N 15/09
See application file for complete search history.

(56) References Cited

U.S. PATENT DOCUMENTS

| RE37,393 E | 9/2001 | Donnelly et al. |
| 2012/0040426 A1 | 2/2012 | Sun et al. |

FOREIGN PATENT DOCUMENTS

| KR | 1995-0026978 A | 10/1995 |
| KR | 1999-0067095 A | 8/1999 |

(Continued)

OTHER PUBLICATIONS

Gilbert et al. Complementation in vitro between guaB mutants of *Escherichia coli* K12. J Gen Microbiol. Mar. 1980;117(1):33-45.*

(Continued)

*Primary Examiner* — Yong Pak
(74) *Attorney, Agent, or Firm* — Hultquist, PLLC; Steven J. Hultquist

(57) ABSTRACT

The present invention relates to mutant microorganisms having a high ability to produce fermentation products, and methods for producing fermentation products using the same, and more particularly, to mutant microorganisms having a high ability to produce fermentation products such as lactic acid, succinic acid and ethanol, which has a deletion of genes selected from the genome of enteric bacteria and involved in respiration, electron transport, redox reactions and the like, and methods of producing fermentation products in high yield by culturing the mutant microorganisms under anaerobic conditions. The present invention provides mutant microorganisms, which have a deletion of genes involved in the redox pathways and regulation of microorganisms and having the property of producing a high concentration of lactic acid, succinic acid or ethanol with significantly reduced production of other fermentation products under anaerobic conditions, and a method of producing lactic acid, succinic acid or ethanol in high yield by culturing the mutant microorganisms.

4 Claims, 5 Drawing Sheets

(51) Int. Cl.
| | |
|---|---|
| C12P 7/56 | (2006.01) |
| C07H 21/04 | (2006.01) |
| C12Q 1/68 | (2006.01) |
| C12N 15/09 | (2006.01) |
| C12P 7/06 | (2006.01) |
| C12P 7/46 | (2006.01) |
| C12N 15/01 | (2006.01) |

(56) References Cited

FOREIGN PATENT DOCUMENTS

| | | |
|---|---|---|
| KR | 10-2005-0057969 A | 6/2005 |
| KR | 10-2005-0102827 A | 10/2005 |
| WO | 2009065778 A1 | 5/2009 |
| WO | 2012055998 A1 | 5/2012 |

OTHER PUBLICATIONS

Chang, D., et al, "Homofermentative production of D- or L-lactate in metabolically engineered *Escherichia coli* RR1", "Applied and Environmental Microbiology", Apr. 1999, pp. 1384-1389, vol. 65, No. 4.

Gupta, S., et al., "*Escherichia coli* Derivatives Lacking Both Alcohol Dehydrogenase and Phosphotransacetylase Grow Anaerobically by Lactate Fermentation", "Journal of Bacteriology", Jul. 1989, pp. 3650-3655, vol. 171, No. 7.

Hofvendahl, K., et al., "Factors affecting the fermentative lactic acid production from renewable resources", "Enzyme and Microbial Technology", 2000, pp. 87-107, vol. 26.

Hujanen, M., et al., "Effect of temperature and various nitrogen sources on L(+)-lactic acid production by Lactobacillus casei", "Appl Microbiol Biotechnol", 1996, pp. 307-313, vol. 45.

Kim, H., et al, "Genome-wide analysis of redox reactions reveals metabolic engineering targets for D-lactate overproduction in *Escherichia coli*", "Metabolic Engineering", Apr. 4, 2013, pp. 44-52, vol. 18.

Miura, S., et al., "Enhanced Production of L-Lactic Acid by Ammonia-Tolerant Mutant Strain *Rhizopus* sp. MK-96/1196", "Journal of Bioscience and Bioengineering", 2004, pp. 19-23, vol. 97, No. 1.

Nizam, S., et al., "Effects of arcA and arcB genes knockout on the metabolism in *Escherichia coli* under anaerobic and microaerobic conditions", "Biochemical Engineering Journal", 2008, pp. 229-236, vol. 42.

Poon, W., et al., "Identification of *Escherichia coli* ubiB, a Gene Required for the First Monooxygenase Step in Ubiquinone Biosynthesis", "Journal of Bacteriology", Sep. 2000, pp. 5139-5146, vol. 182, No. 18.

Saitoh, S., et al., "Genetically Engineered Wine Yeast Produces a High Concentration of L-Lactic Acid of Extremely High Optical Purity", "Applied and Environmental Microbiology", May 2005, pp. 2789-2792, vol. 71, No. 5.

Yang, C., et al., "Lactic Acid Production by Pellet-Form Rhizopus oryzae in a Submerged System", "Applied Biochemistry and Biotechnology", 1995, pp. 57-71, vol. 51/52.

Zhou, S., et al., "Production of Optically Pure D-Lactic Acid in Mineral Salts Medium by Metabolically Engineered *Escherichia coli* W3110", "Applied and Environmental Microbiology", Jan. 2003, pp. 399-407, vol. 69, No. 1.

Zhu, J., et al., "Effect of the global redox sensing/regulation networks on *Escherichia coli* and metabolic flux distribution based on C-13 labeling experiments", "Metabolic Engineering", Aug. 7, 2006, pp. 619-627, vol. 8.

\* cited by examiner (A) Control of metabolic fluxes by regulation of respiration (B) Selection of single-gene-deleted strains for anaerobic fermentation S, L, A, E and F indicate succinate, lactate, acetate, ethanol and formate, respectively. Numeral indicates concentration (mM) of fermentation metabolites produced under anaerobic conditions.

VARIANT MICROORGANISM ABLE TO PRODUCE LARGE AMOUNT OF FERMENTATION PRODUCT, AND FERMENTATION PRODUCT PRODUCTION METHOD USING SAME

CROSS-REFERENCE TO RELATED APPLICATIONS

This application is a U.S. national phase under the provisions of 35 U.S.C. §371 of International Patent Application No. PCT/KR13/005285 filed Jun. 15, 2013, which in turn claims priority of Korean Patent Application No. 10-2012-0064525 filed Jun. 15, 2012. The disclosures of such international patent application and the Korea priority patent application are hereby incorporated herein by reference in their respective entireties, for all purposes.

TECHNICAL FIELD

The present invention relates to mutant microorganisms having a high ability to produce fermentation products, and methods for producing fermentation products using the same, and more particularly, to mutant microorganisms having a high ability to produce fermentation products such as lactic acid, succinic acid and ethanol, which have a deletion of genes selected from the genome of enteric bacteria and involved in respiration, electron transport, redox reactions and the like, and methods of producing fermentation products in high yield by culturing the mutant microorganisms under anaerobic conditions.

BACKGROUND ART

As environmental problems such as climate change have recently emerged and the exhaustion of petroleum resources is expected to be depleted, attempts to produce most compounds by biotechnology as an alternative to chemical processes have been made, and the need for the development of related technology has increased. In addition, because of high petroleum prices, the production of compounds by microbial metabolisms and biological processes is becoming more price-competitive with petrochemical processes. Thus, the demand for the development of microbial strains and fermentation techniques that can solve energy problems is highly increasing. Among various biochemical compounds, lactic acid can be used in various applications, including a monomer for polylactic acid (PLA) that is a biodegradable polymer, a food additive, a precursor for drugs, etc., and has been of increasing interest.

Microorganisms reported to be used for the biological production of lactic acid (*Appl. Microbiol. Biotechnol.*, 45, 307, 1996; *Enzyme Microb. Technol.*, 26, 87, 2000; Korean Patent Application No. 10-2003-0090204) include lactic acid bacteria of the genus *Lactobacillus* and the genus *Lactococcus*, fungi of the *Rhizopus* (*Appl. Biochem. Biotechnol.*, 51, 57, 1995; *J. Biosci. Bioeng.*, 97, 19, 2004), yeasts of the genus *Saccharomyces* (*Appl. Environ. Microbiol.*, 71, 2789, 2005), and *E. coli*. Lactic acid bacteria have a shortcoming in that the lactic acid produced has low optical purity, because it is a mixture of D- and L-forms. Fungi have a shortcoming in that large amounts of byproducts such as glycerol and ethanol are produced. Yeasts have shortcomings in that a large amount of ethanol is produced as a byproduct and in that lactic acid is produced in low yield.

In connection with the production of lactic acid in *E. coli*, it was reported that a mutant strain with a deletion of alcohol dehydrogenase (adhE) and phosphotrans acetylase (pta) genes produces lactic acid (*J. Bacteriol.* 171, 3650, 1989). In addition, there are known a method of using a mutant strain having a deletion of alcohol dehydrogenase (adhE) gene and phosphoenolpyruvate carboxylase (ppc) genes (*Appl. Environ. Microbiol.*, 65, 1384, 1999); Korean Patent Application No. 1994-0004034), and a method of using pyruvate formate-lyase (pfl), fumarate reductase (frdABCD), alcohol dehydrogenase (adhE) and acetate kinase (ack) genes. Also, it is known that a mutant microorganism with a ubiquinone biosynthetic gene mutation accumulates lactic acid (*Appl. Environ. Microbiol.*, 69, 399, 2003). Moreover, it was reported that deletion of the fnr gene (encoding a transcriptional regulator) and arcBA genes (encoding two-component response regulators) of *E. coli* leads to an increase in the production of lactic acid (Biochemical Engineering J. 42, 229-236, 2008), and the analysis of the metabolic carbon flux in mutant strains having a deletion of one or more of these genes indicated that the production of lactic acid increased (*Metabolic engineering* 8, 619-627, 2006). Known methods related to the production of lactic acid in *E. coli* are mostly performed using improved fermentation processes and mutant strains that have a deletion of the above-described known genes.

Currently, with the rapid exploitation of microbial genome information through new next-generation sequencing technology and the development of omics technology, platform technology capable of investigating microbial physiology and metabolism at the system level is being provided, but the functions and interactions of microbial genes have not yet been sufficiently elucidated. Organic acids and ethanol, which are produced during microbial fermentation which involves electron transfer and rearrangement, and this fermentation process is performed while maintaining the intracellular redox balance. In this process, oxidoreductases play an important role. A large number of oxidoreductases are present in the microbial genome, and networks regarding the connection between oxidoreductases are not sufficiently known.

The present inventors have found that enzymatic genes controlling the redox balance in an unknown respiratory system can control the metabolic flux of carbon by controlling the redox balance, and have identified genes playing an important role in the production of lactic acid, succinic acid or ethanol in the metabolic flux of carbon. Accordingly, the present inventors have made efforts to develop strains that highly produce lactic acid, succinic acid or ethanol, respectively, and as a result, have found that lactic acid, succinic acid or ethanol can be produced in high yield by preparing mutant strains wherein one or more of oxidoreductase genes and regulatory genes are inactivated or deleted, and culturing the prepared mutant strains. Based on this finding, the present invention has been completed.

DISCLOSURE OF INVENTION

Technical Problem

It is a main object of the present invention to reconstitute the redox balance by anaerobically fermenting mutant strains having a deletion of each of 472 genes, selected from the genome and involved in respiration, electron transfer and redox reactions at the genome level, and to select genes capable of controlling the metabolic carbon flux from the above 472 genes, and also to provide mutant microorganisms that overproduce lactic acid, succinic acid or ethanol with significantly reduced production of other organic acids, and a method for preparing the mutant microorganisms.

Another object of the present invention is to provide a method of producing lactic acid, succinic acid or ethanol in high yield by culturing the mutant microorganisms.

TECHNICAL SOLUTION

To achieve the above objects, the present invention provides a mutant microorganism having the ability to produce lactic acid wherein one or more oxidoreductase genes selected from the group consisting of an inosine-5-phosphate dehydrogenase encoding gene (guaB), a D-3-phosphoglycerate dehydrogenase encoding gene (serA) and a dihydroorotate dehydrogenase encoding gene (pyrD), which are involved in the amino acid and nucleic acid biosynthesis pathways of a microorganism, are inactivated or deleted.

The present invention also provides a method for preparing a mutant microorganism having the ability to produce lactic acid wherein one or more oxidoreductase genes selected from the group consisting of an inosine-5-phosphate dehydrogenase encoding gene (guaB), a D-3-phosphoglycerate dehydrogenase encoding gene (serA) and a dihydroorotate dehydrogenase encoding gene (pyrD), which are involved in the amino acid and nucleic acid biosynthesis pathways of a microorganism, are inactivated or deleted.

The present invention also provides a method for producing lactic acid, the method comprising the steps of: culturing the above-described mutant microorganisms to produce lactic acid; and recovering lactic acid from the culture broth.

The present invention also provides mutant microorganisms having the ability to produce succinic acid wherein one or more genes selected from the group consisting of a predicted semialdehyde dehydrogenase encoding gene (usg), a formate dehydrogenase H encoding gene (fodH), a glycerol-3-phosphate dehydrogenase encoding gene (glpC), a 6-phosphogluconate dehydrogenase encoding gene (gnd), an L-idonate-5-dehydrogenase encoding gene (idnD), a hydrogenase G encoding gene (hyfG), a predicted oxidoreductase encoding gene (ybdH), a pyrroline-5-carboxylate reductase encoding gene (proC), a hydrogenase C encoding gene (hyfC), a phosphoglycolate phosphatase encoding gene (gph) and a dihydrolipoyl transsuccinylase encoding gene (sucB), which are involved in the redox pathways and regulation of a microorganism, are inactivated or deleted.

The present invention also provides a method for preparing mutant microorganisms having the ability to produce succinic acid wherein one or more genes selected from the group consisting of a predicted semialdehyde dehydrogenase encoding gene (usg), a formate dehydrogenase H encoding gene (fodH), a glycerol-3-phosphate dehydrogenase encoding gene (glpC), a 6-phosphogluconate dehydrogenase encoding gene (gnd), an L-idonate-5-dehydrogenase encoding gene (idnD), a hydrogenase G encoding gene (hyfG), a predicted oxidoreductase encoding gene (ybdH), a pyrroline-5-carboxylate reductase encoding gene (proC), a hydrogenase C encoding gene (hyfC), a phosphoglycolate phosphatase encoding gene (gph) and a dihydrolipoyl transsuccinylase encoding gene (sucB), which are involved in the redox pathways and regulation of a microorganism, are inactivated or deleted.

The present invention also provides a method for producing succinic acid, the method comprising the steps of: culturing the above-described mutant microorganisms to produce succinic acid; and recovering succinic acid from the culture broth.

The present invention also provides mutant microorganisms having the ability to produce ethanol wherein one or more genes selected from the group consisting of a 3-isopropylmalate dehydrogenase encoding gene (leuB), a thioredoxin encoding gene (trxA), a pyruvate dehydrogenase complex transcriptional regulator encoding gene (pdhR), a formate dehydrogenase H encoding gene (fdnH) and a NADH-ubiquinone oxidoreductase complex ABCEFGHIJKLN encoding gene (nuoABCEFGHIJKLN), which are involved in the redox pathways and regulation of a microorganism, are inactivated or deleted.

The present invention also provides a method for preparing mutant microorganisms having the ability to produce ethanol wherein one or more genes selected from the group consisting of a 3-isopropylmalate dehydrogenase encoding gene (leuB), a thioredoxin encoding gene (trxA), a pyruvate dehydrogenase complex transcriptional regulator encoding gene (pdhR), a formate dehydrogenase H encoding gene (fdnH) and a NADH-ubiquinone oxidoreductase complex ABCEFGHIJKLN encoding gene (nuoABCEFGHIJKLN), which are involved in the redox pathways and regulation of a microorganism, are inactivated or deleted.

The present invention also provides a method for producing ethanolethanol, the method comprising the steps of: culturing the above-described mutant microorganisms to produce ethanol; and recovering ethanol from the culture broth.

BEST MODE FOR CARRYING OUT THE INVENTION

As used herein, the term "inactivating" or "inactivated" is meant to comprehend the mutation, substitution (replacement) or deletion of one or more bases of a target gene or the introduction of one or more bases into the gene, so as to reduce the activity of an enzyme which is expressed by the gene, thereby partially or wholly blocking the biosynthetic pathway in which the enzyme is involved.

As used herein, the term "deleting" or "deleted" is meant to comprehend the mutation, substitution (replacement) or deletion of the whole or a part of a target gene or the introduction of one or more bases into the gene, so that the gene is not expressed or does not exhibit enzymatic activity, and further, so that, even though it is expressed, the gene-associated biosynthetic pathway is blocked.

The present invention relates to a new system metabolic engineering technology of preparing a mutant microorganism by deleting genes, selected at the genome level and involved in respiration, electron transfer and redox reactions, to enhance the ability to produce a desired fermentation product. Specifically, unlike a conventional system metabolic engineering technology of controlling metabolic fluxes by blocking competitive metabolic pathways and amplifying directly related metabolic networks, the present invention relates to a technology of deleting enzymes and transcription regulatory genes, which are not involved directly in carbon metabolic pathways that produce lactic acid, succinic acid, ethanol and the like, thereby preparing mutant microorganisms having an increased ability to produce lactic acid, succinic acid, ethanol and the like.

Figure 1:
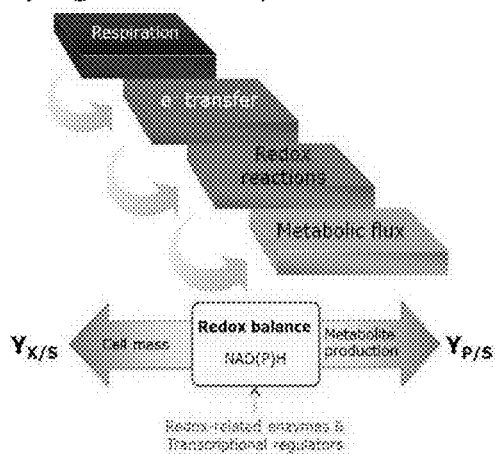
FIG. 1 shows a process for selecting single-gene-deleted mutant microorganisms that control metabolic flux by regulating cellular respiration.
Figure 1:
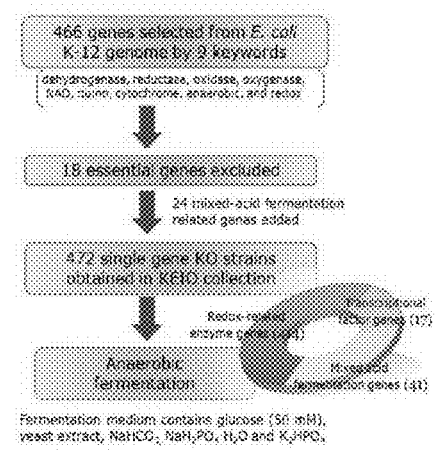

FIG. 1 shows a process for selecting single-gene-deleted mutant microorganisms that control metabolic flux by regulating respiration. As shown in FIG. 1, in the present invention, mutant microorganisms having a deletion of each of the respiration-related and redox-related genes of microorganisms were cultured under anaerobic conditions, and then the relationship between the anaerobic metabolism and energy metabolism of each mutant microorganism was analyzed based on the growth of each microbial strain and the production of final fermentation products therein. As genes for analysis, a total of 472 genes were selected by performing a search in http://www.ncbi.nlm.nih.gov/COG/ by 9 keywords, including dehydrogenase, reductase, oxidase, oxygenase, NAD, quino, cytochrome, anaerobic, and redox. Mutants lacking each of the selected genes were obtained from the KEIO collection in a state in which each gene was replaced with a kanamycin resistance gene.

Each of a total of 472 single-gene-deleted microbial strains was plated on an antibiotic-containing medium, and cultured under anaerobic conditions while the growth of the strains and the production of fermentation products therein were analyzed. As a result, it could be seen that, when each of an inosine-5-phosphate dehydrogenase encoding gene (guaB), a D-3-phosphoglycerate dehydrogenase encoding gene (serA) and a dihydroorotate dehydrogenase encoding gene (pyrD), a fumarate nitrate reductase transcriptional regulator encoding gene (fnr), a aerobic respiration control response regulator encoding gene (arcA) and an aerobic respiration control sensor kinase encoding gene (arcB), was deleted, the production of lactic acid by anaerobic fermentation increased, whereas the production of other fermentation products decreased.

In one aspect, the present invention is directed to a mutant microorganism having the ability to produce lactic acid wherein one or more oxidoreductase genes selected from the group consisting of an inosine-5-phosphate dehydrogenase encoding gene (guaB), a D-3-phosphoglycerate dehydrogenase encoding gene (serA) and a dihydroorotate dehydrogenase encoding gene (pyrD), which are involved in the amino acid and nucleic acid biosynthesis pathways of a microorganism, are inactivated or deleted, and a method for preparing the mutant microorganism.

In the present invention, the mutant microorganism is characterized in that one or more genes selected from the group consisting of a fumarate nitrate reductase transcriptional regulator encoding gene (fnr), an aerobic respiration control response regulator encoding gene (arcA), and an aerobic respiration control sensor kinase encoding gene (arcB) are further inactivated or deleted.

In the present invention, deletion of each gene was performed by substituting and inactivating the gene by homologous recombination using the P1 transduction method, but any genetic manipulation method may be used without limitations, as long as it can modify or delete the gene of interest so that an enzyme encoded by the gene of interest is not produced.

In the present invention, the microorganism may be used without limitations as long as it is an enteric bacterium. Examples of the enteric bacterium include *Escherichia* sp., *Salmonella* sp., *Erwinia* sp., *Yersinia* sp., *Shigella* sp., *Klebsiella* sp., *Proteus* sp. and the like. More specifically, an example of *Escherichia* sp. may be BW25113 (*Escherichia coli* BW25113) or the like.

The mutant microorganism according to the present invention has the property of producing lactic acid at high concentrations under anaerobic conditions while producing other fermentation products at significantly low concentrations.

In another aspect, the present invention is directed to a method for producing lactic acid, the method comprising the steps of: culturing a mutant microorganism to produce lactic acid; and recovering lactic acid from the culture.

In the present invention, the culture of the mutant microorganism and the recovery of lactic acid from the culture broth can be carried out using a culture method (batch culture or fed-batch culture) known in conventional fermentation processes, and lactic acid separation and purification methods known in the art.

In the present invention, the medium that is used in the culture is not specifically limited, but the initial concentration of glucose in the medium is preferably 8-20 g/L, and most preferably 9 g/L. The culture may be performed at a temperature of preferably 35-45° C., preferably 35-39° C., most preferably 37° C., and an initial pH of 7.0-9.5, most preferably 8.7. In addition, the culture is preferably performed under anaerobic conditions, and the anaerobic conditions can be formed by feeding nitrogen into the head space of an incubator and adding $Na_2S$ thereto to remove dissolved oxygen. The incubator is not specifically limited, but may be a serum bottle.

In addition, in the present invention, as described above, it could be found that when one or more genes selected from the group consisting of a predicted semialdehyde dehydrogenase encoding gene (usg), a formate dehydrogenase H encoding gene (fodH), a glycerol-3-phosphate dehydrogenase encoding gene (glpC), a 6-phosphogluconate dehydrogenase encoding gene (gnd), an L-idonate-5-dehydrogenase encoding gene (idnD), a hydrogenase G encoding gene (hyfG), a predicted oxidoreductase encoding gene (ybdH), a pyrroline-5-carboxylate reductase encoding gene (proC), a hydrogenase C encoding gene (hyfC), a phosphoglycolate phosphatase encoding gene (gph) and a dihydrolipoyl transsuccinylase encoding gene (sucB), which are involved in the redox pathways and regulation of a microorganism, are inactivated or deleted, the ability of the mutant microorganism to produce succinic acid increased.

Also, in the present invention, it could be found that when one or more genes selected from the group consisting of a 3-isopropylmalate dehydrogenase encoding gene (leuB), a thioredoxin encoding gene (trxA), a pyruvate dehydrogenase complex transcriptional regulator encoding gene (pdhR), a formate dehydrogenase H encoding gene (fdnH) and a NADH-ubiquinone oxidoreductase complex ABCEFGHIJKLN encoding gene (nuoABCEFGHIJKLN), which are involved in the redox pathways and regulation of a microorganism, are inactivated or deleted, the ability of the mutant microorganism to produce ethanol increased.

In addition, the present inventors disclosed the content of the present invention in Korean Patent Application No.

2012-0064525 (Jun. 15, 2012), and then published it as an article entitled "Genome-wide analysis of redox reactions reveals metabolic engineering targets for D-lactate overproduction in *Escherichia coli*" in Metabolic Engineering that is a journal related to microbial metabolic engineering (*Metabolic Engineering* 18, 44-5, 2013).

In addition, the following Examples illustrate only a specific medium and culture method, it will be obvious to those skilled in the art to use hydrolysates such as whey or CSL (corn steep liquor), or other media, or to use various culture methods such as fed-batch culture or continuous culture.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Anaerobic Fermentation of Single-Gene-Deleted Mutant Strains and Analysis of Organic Acids Mutant microorganisms having a deletion of each of the respiration-related and redox-related genes of microorganisms were cultured under anaerobic conditions, and then the relationship between the anaerobic metabolism and energy metabolism of each mutant microorganism was analyzed based on the growth of each microbial strain and the production of final fermentation products therein. As genes for analysis, a total of 472 genes were selected by performing a search in http://www.ncbi.nlm.nih.gov/COG/ by 9 keywords, including dehydrogenase, reductase, oxidase, oxygenase, NAD, quino, cytochrome, anaerobic, and redox. Mutants lacking each of the selected genes were obtained from the KEIO collection in a state in which each gene was replaced with a kanamycin resistance gene (FIG. 1).

Each of a total of 472 single-gene-deleted mutant strains was plated on an LB solid medium containing kanamycin (25 μg/ml), and the grown single colony was seeded into 5 ml of an LB liquid medium and pre-cultured at 37° C. for 12 hours. 1 ml of the strain culture was seeded into a 125-ml serum bottle containing 100 ml of a fermentation medium (per liter, 9 g glucose (final 50 mM), 5 g yeast extract, 10 g $NaHCO_3$; 8.5 g $NaH_2PO_4*H_2O$, 15.5 g $K_2HPO_4$ (pH8.7)), and 1 mM of $Na_2S$ was added thereto. Then, the bottle was sealed, and the upper portion thereof was charged with nitrogen gas to remove oxygen from the serum bottle, after which each strain was cultured at 37° C. for 24 hours.

For analysis of strain growth and final fermentation products, 5 ml was taken from each of the cultures of the anaerobically cultured strains, and 1 ml of each of the taken cultures was diluted in PBS at a ratio of 1:10. The $OD_{600}$ value of each dilution was measured to determine the growth of each strain. 4 ml of each of the remaining cultures was centrifuged at 5000 rpm for 5 minutes, and filtered through a 0.2 ml nylon filter. 1 ml of each filtrate was analyzed by HPLC. Organic acids (glucose, succinic acid, lactic acid, formic acid, acetic acid and ethanol) were analyzed using Aminex HPX-87H Column (Bio-Rad) and 0.01N $H_2SO_4$ solution as a mobile phase.

Figure 2:
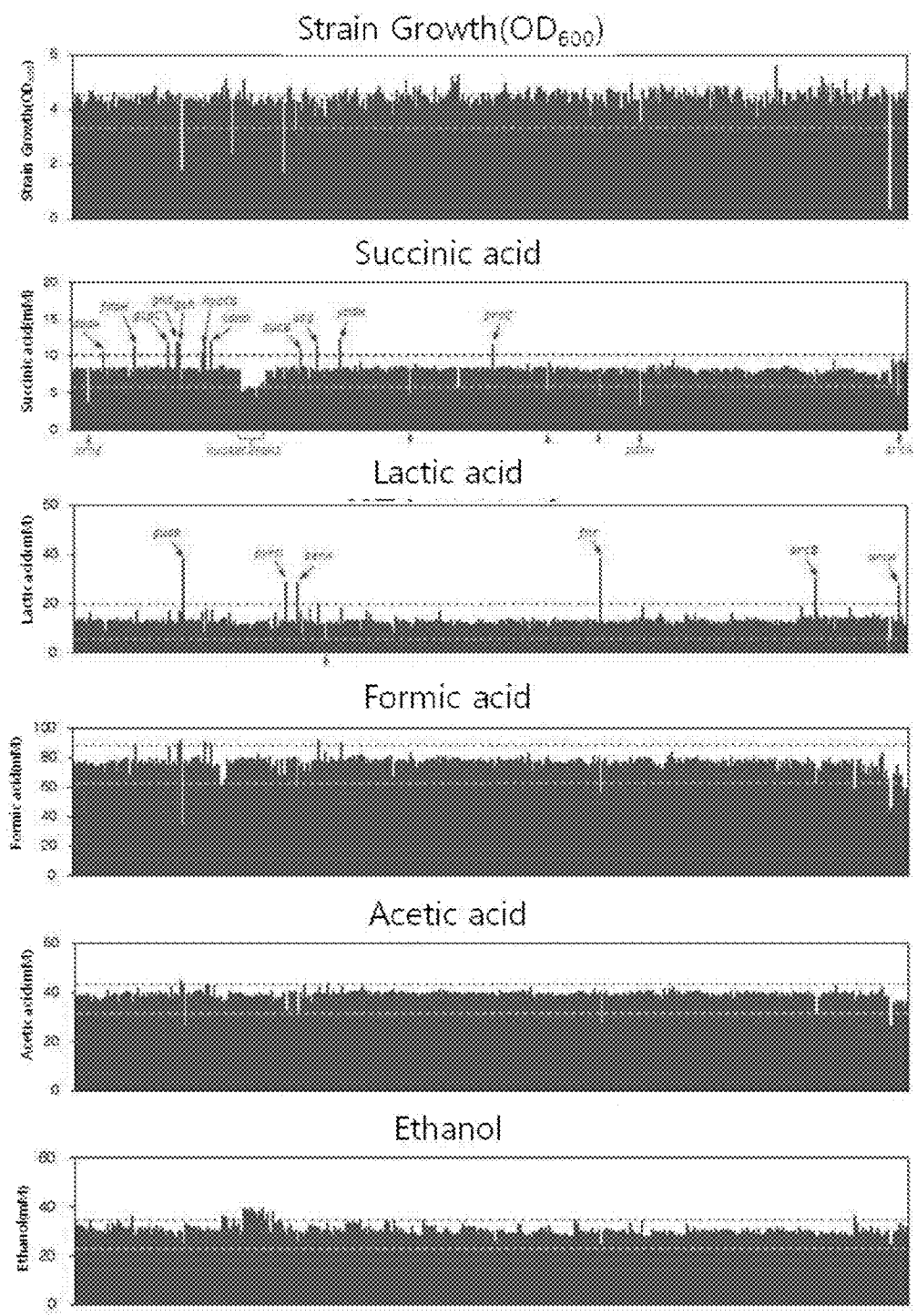
FIG. 2 shows the growth profile of 431 single-gene-deleted mutant microorganisms and the production of fermentation products therein.

In order to select mutant strains that overproduce useful fermentation products such as lactic acid, succinic acid and ethanol, the growth of the 472 selected mutant strains a single gene deletion and the production of final fermentation products therein were analyzed. Final fermentation products in 431 single-gene-deleted mutant strains, excluding 41 mutant strains related directly to carbon metabolism, are shown in FIG. 2.

The production of final fermentation products in the 431 single-gene-deleted mutant strains was statistically processed, and then the single genes whose deletion showed a significant increase or decrease in the production of fermentation products were examined. The results are shown in Table 1. Based on the results, the redox balance in intracellular anaerobic respiration conditions can be reconstituted. Based on this reconstitution, genes capable of controlling the metabolic flux of carbon can be selected, and information on genes that control various fermentation products such as lactic acid, succinic acid and ethanol can be obtained.

TABLE 1

| Fermentation products | Succinic acid (mM) | Lactic acid (mM) | Formic acid (mM) | Acetic acid (mM) | Ethanol (mM) |
|---|---|---|---|---|---|
| Production of final fermentation products in wild-type strains | 10.05 | 13.95 | 61.00 | 37.00 | 34.91 |
| Mean ± SD* | 8.12 ± 0.95 | 13.20 ± 2.84 | 76.86 ± 5.18 | 39.37 ± 1.84 | 30.64 ± 2.18 |
| Genes[†] decreasing the production of fermentation products due to deletion | fnr, arcA, zwf, pdxH, ygiR, ssuD, aroE, nuoABCEFGHIJKLN | xdhB | fnr, guaB, serA, arcB, oxyR, glcE, leuB, lldD, trxA, soxS | fnr, guaB, serA, arcB, pyrD, oxyR | fnr |
| Genes[†] increasing the production of fermentation products due to deletion | usg, fodH, glpC, gnd, idnD, hyfG, ybdH, proC, | fnr, arcA, guaB, serA, arcB, pyrD | usg, gph, hyfG, ybdH | gnd | leuB, trxA, pdhR, fdnH, nuoABCEFGHIJKLN |

TABLE 1-continued

| Fermentation products | Succinic acid (mM) | Lactic acid (mM) | Formic acid (mM) | Acetic acid (mM) | Ethanol (mM) |
|---|---|---|---|---|---|
| | hyfC, gph, sucB | | | | |

*Mean ± SD indicates the concentration of each fermentation product in 472 single-gene-deleted mutant strains related to redox.
†indicates genes whose deletion shows at least 2.5 times increase or decrease in the production of each fermentation product compared to the SD value.

Figure 3:
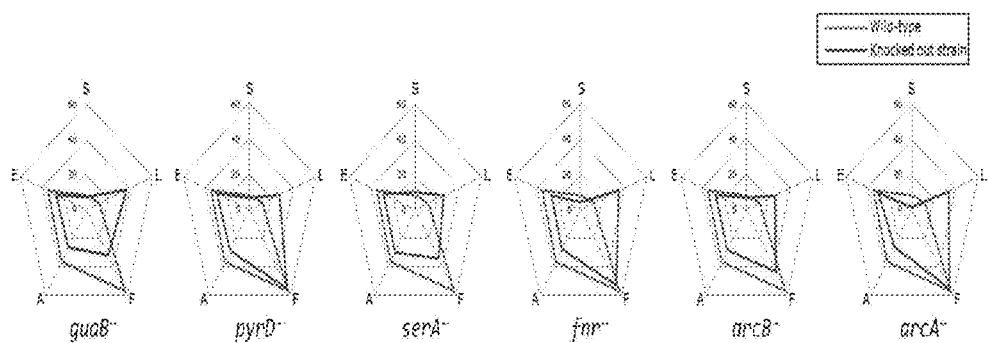
FIG. 3 shows the results of analysis of fermentation products in lactic acid-overproducing mutant strains having a deletion of each of selected single genes.

As can be seen in Table 1 above, when each of the fnr, arcB, arcA, serA, pyrD and guaB genes was deleted, the production of lactic acid by anaerobic fermentation increased, and the production of other fermentation products relatively decreased (FIG. 3).

In addition, it was shown that, when each of the usg, fodH, glpC, gnd, idnD, hyfG, ybdH, proC, hyfC, gph and sucB genes was deleted, the production of succinic acid by anaerobic fermentation increased, whereas the production of other fermentation products decreased. Additionally, it was shown that, when each of the leuB, trxA, pdhR, fdnH and nuoABCEFGHIJKLN genes was deleted, the production of ethanol by anaerobic fermentation increased, whereas the production of other fermentation products decreased.

Example 2

Construction of Single-Gene-Deleted Mutant Strains by P1 Transduction and Confirmation of Increased Production of Lactic Acid In order to accurately examine whether the anaerobic fermentation property of each single-gene-deleted mutant strain selected as a lactic acid-overproducing mutant strain is attributable to deletion of the selected gene, each of the selected fnr, arcA, arcB, serA, pyrD and guaB genes was introduced into each of wild-type recipient strains [BW25113 (CGSC7636, The Coli Genetic Stock Center, Yale University) and MG1655 (ATCC700926, American Type Culture Collection)] by P1 transduction, and each of the strains was anaerobically cultured. Then, final fermentation products (organic acids) in the strains were compared with those in the wild-type strains. As a result, it could be seen that the increase in the production of lactic acid in each mutant strain was caused by deletion of each gene.

TABLE 2

| | Gene-deleted mutant strains obtained from KEIO collection | The case where mutant strains are introduced into wild-type strain MG1655 | The case where mutant strains are introduced into wild-type strain BW25113 |
|---|---|---|---|
| Wild-type | 12.87* | 15.73# | 12.00* |
| guaB⁻ | 38.23 | 24.37 | 20.32 |
| pyrD⁻ | 28.99 | 28.41 | 27.74 |
| serA⁻ | 28.94 | 32.34 | 32.82 |
| fnr⁻ | 38.65 | 32.96 | 34.69 |
| arcB⁻ | 30.11 | 29.67 | 29.16 |
| arcA⁻ | 27.71 | 21.66 | 27.08 |

Comparison of lactic acid production (mM) after introduction of each gene deletion into each strain
*wild type strain BW25113.
wild type strain MG1655.

P1 transduction was performed in the following manner. First, each mutant strain having a replacement of each of single genes (fnr, arcB, arcA, serA, pyrD and guaB) by a kanamycin resistance gene was obtained from the KEIO collection, and plated on an LB solid medium containing 25 µg/ml of kanamycin. Each grown colony was seeded into 25 me of an LB liquid medium (containing 0.01M MgSO₄ and 0.005M CaCl₂), and cultured at 37° C. until it reached an $OD_{600}$ of 0.4. Next, 250 µl of P1 bacteriophage was inoculated into each culture, which was then cultured at 37° C. for 4 hours to lyse each mutant strain. After culture, 500 µl of chloroform was added to each culture, and then centrifuged at 3000 rpm for 10 minutes. Next, each supernatant excluding the lysed cell pellet was collected, and it was used as a P1 lysate for single gene deletion, obtained by lysis of each mutant strain by P1 bacteriophages.

Each of wild-type recipient strains [BW25113 (CGSC7636, The Coli Genetic Stock Center, Yale University) and MG1655(ATCC700926, American Type Culture Collection)], into which a gene deletion was to be transduced by the prepared P1 lysates, was seeded into an LB liquid medium (containing 0.01M MgSO₄ and 0.005M CaCl₂) and cultured, after which each culture was centrifuged at 5000 rpm. The medium was removed, and the cell pellet was suspended in 1 me of an LB liquid medium containing 0.01M MgSO₄ and 0.005M CaCl₂.

100 µl of the prepared P1 lysate for gene deletion was mixed with 100 µl of the culture of recipient strains, and then incubated at 37° C. for 20 minutes, and 100 µl of 1M Na⁺.Citrate.2H₂O was added thereto and well mixed. The mixture was plated on an LB solid medium containing 25 ug/ml of kanamycin, and was incubated at 37° C., thereby constructing strains having introduced therein each gene deletion portion replaced with kanamycin resistance.

Example 3

Construction of Mutant Strains Having Deletion of Two or More Genes

In order to examine whether deletion of two or more of the selected fnr, arcB, arcA, serA, pyrD and guaB genes contributes to an increase in the production of lactic acid, mutant strains having a deletion of two or more genes were constructed by introducing each gene deletion into a strain having another gene deletion by transduction using P1 lysate. In this Example, a process of preparing P1 lysate from each single-gene-deleted mutant is as described in Example 2, and a process of preparing a recipient strain into which a gene deletion is to be introduced is as follows. Each single-gene-deleted mutant strain was transformed with a pCP20 plasmid (CGSC7629, The Coli Genetic Stock Center, Yale University), and plated on an LB solid medium (containing 50 µg/ml of ampicillin) to induce homologous recombination, thereby constructing recipient strains having a deletion of the kanamycin resistance gene. The recipient strains had a deletion of each of the selected genes, but had no kanamycin resistance. One or more other gene deletions were introduced into each recipient strain by transduction using P1 lysate, thereby constructing mutant strains having a deletion of two or more of the selected genes.

Figure 4:
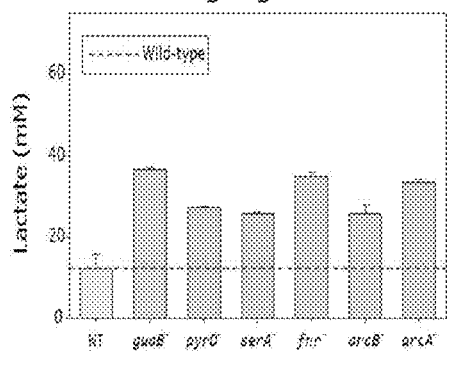
FIG. 4 shows the production amount (mM) of lactic acid in mutant strains having a deletion of single genes and a deletion of two or more genes.
Figure 4:
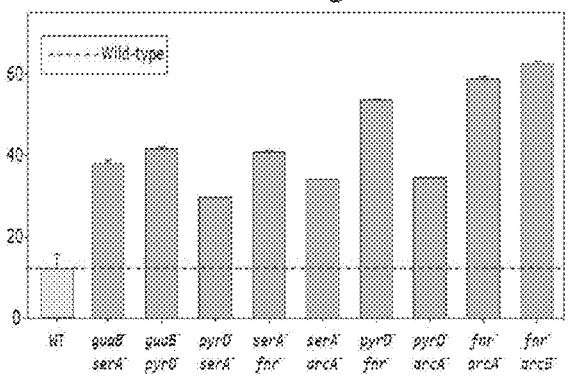
Figure 5:
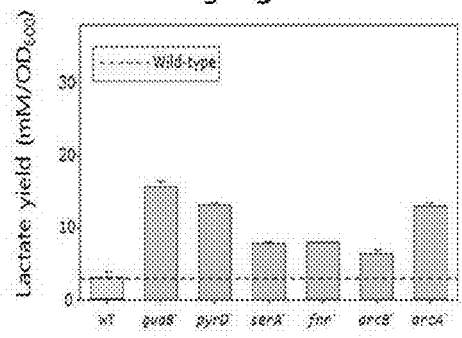
FIG. 5 shows the production yield (mM/OD) of lactic acid in mutant microorganisms having a deletion of single genes and a deletion of two or more genes.
Figure 5:
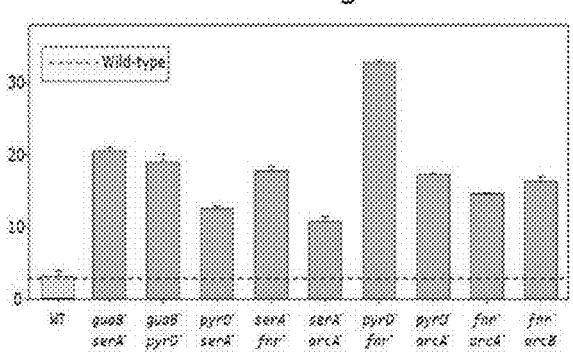

The production amount and yield of lactic acid in each of the mutant strains of Example 1, which have a single gene deletion, and the mutant strains of Example 3, which have a deletion of two or more genes, are shown in FIGS. 4 and 5 and Table 3 below.

As shown in FIGS. 4 and 5, the production amount and yield of lactic acid in the mutant strains having a deletion of two or more genes was generally higher than that in the mutant strains having a single gene deletion. The production amount of lactic acid in the mutant strain having a deletion of both fnr and arcB reached 62.5 mM, which was 4.8 times higher than that in the wild-type strain (FIG. 4). In addition, the production yield of lactic acid in the mutant strain having a deletion of both pyrD and fnr was 10.6 times higher than that in the wild-type strain (FIG. 5).

Thus, it was found that the deletion of one or more of the genes selected from the genome of microorganisms led to an increase in the production of lactic acid.

TABLE 3

| | Production of lactic acid (mM) | Yield of lactic acid (mM/OD$_{600}$) | Production of lactic acid (g/L) | Yield (lactic acid (g)/glucose (g)) |
|---|---|---|---|---|
| BW25113 | 12.16 (1.0) | 3.08 (1.0) | 1.09 (1.0) | 0.12 |
| guaB⁻ | 36.65 (3.0) | 15.66 (5.1) | 3.30 (3.0) | 0.37 |
| pyrD⁻ | 27.36 (2.3) | 13.16 (4.3) | 2.46 (2.3) | 0.27 |
| serA⁻ | 25.75 (2.1) | 7.85 (2.6) | 2.32 (2.1) | 0.26 |
| fnr⁻ | 34.83 (2.9) | 7.91 (2.6) | 3.13 (2.9) | 0.35 |
| arcB⁻ | 25.68 (2.1) | 6.33 (2.1) | 2.31 (2.1) | 0.26 |
| arcA⁻ | 33.54 (2.8) | 12.96 (4.2) | 3.02 (2.8) | 0.34 |
| guaB⁻, serA⁻ | 38.07 (3.1) | 20.51 (6.7) | 3.43 (3.1) | 0.38 |
| guaB⁻, pyrD⁻ | 41.58 (3.4) | 19.03 (6.2) | 3.74 (3.4) | 0.42 |
| pyrD⁻, serA⁻ | 29.58 (2.4) | 12.61 (4.1) | 2.66 (2.4) | 0.30 |
| serA⁻, fnr⁻ | 40.82 (3.4) | 17.72 (5.8) | 3.67 (3.4) | 0.41 |
| serA⁻, arcA⁻ | 34.11 (2.8) | 10.80 (3.5) | 3.07 (2.8) | 0.34 |
| pyrD⁻, fnr⁻ | 53.49 (4.4) | 32.75 (10.6) | 4.81 (4.4) | 0.53 |
| pyrD⁻, arcA⁻ | 34.56 (2.8) | 17.31 (5.6) | 3.11 (2.8) | 0.35 |
| fnr⁻, arcA⁻ | 58.65 (4.8) | 14.65 (4.8) | 5.28 (4.8) | 0.59 |
| fnr⁻, arcB⁻ | 62.47 (5.1) | 16.33 (5.3) | 5.62 (5.1) | 0.62 |

Parentheses indicate an increase (fold) compared to wild-type strain

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described above, the present invention provides mutant microorganisms, which have a deletion of genes involved in the redox pathways and regulation of microorganisms and having the property of producing a high concentration of lactic acid, succinic acid or ethanol with significantly reduced production of other fermentation products under anaerobic conditions, and a method of producing lactic acid, succinic acid or ethanol in high yield by culturing the mutant microorganisms.

In particular, the mutant microorganisms that overproduce lactic acid under anaerobic conditions can be used as a strain for producing biopolymers such as PLA (polylactic acid), and the mutant microorganisms that overproduce succinic acid under anaerobic conditions can be used as a strain for producing biopolymers. In addition, the mutant microorganisms that overproduce ethanol under anaerobic conditions can be used as a strain for producing biofuels.

The invention claimed is:

1. A mutant *Escherichia coli* having the ability to produce lactic acid, wherein one or more oxidoreductase genes selected from the group consisting of an inosine-5-phosphate dehydrogenase encoding gene (guaB), a D-3-phosphoglycerate dehydrogenase encoding gene (serA) and a dihydroorotate dehydrogenase encoding gene (pyrD), which are involved in the amino acid and nucleic acid biosynthesis pathways of *Escherichia coli*, are inactivated or deleted, and wherein one or more genes selected from the group consisting of a fumarate nitrate reductase transcriptional regulator encoding gene (fnr), a aerobic respiration control response regulator encoding gene (arcA), and an aerobic respiration control sensor kinase encoding gene (arcB) are inactivated or deleted.

2. A method for preparing a mutant *Escherichia coli* having the ability to produce lactic acid, comprising inactivating or deleting one or more oxidoreductase genes selected from the group consisting of an inosine-5-phosphate dehydrogenase encoding gene (guaB), a D-3-phosphoglycerate dehydrogenase encoding gene (serA) and a dihydroorotate dehydrogenase encoding gene (pyrD), which are involved in the amino acid and nucleic acid biosynthesis pathways of *Escherichia coli*, and further comprising inactivating or deleting one or more genes selected from the group consisting of a fumarate nitrate reductase transcriptional regulator encoding gene (fnr), a aerobic respiration control response regulator encoding gene (arcA) and an aerobic respiration control sensor kinase encoding gene (arcB).

3. A method for producing lactic acid, the method comprising the steps of: culturing the mutant *Escherichia coli* of claim 1 to produce lactic acid; and recovering lactic acid from the culture.

4. The method of claim 3, wherein the culturing is performed at a temperature of 35-45° C. and an initial pH of 7.0-9.5 under the conditions formed by feeding nitrogen or air containing nitrogen.

* * * * *